United States Patent [19]

Schlueter et al.

[11] 4,393,141

[45] Jul. 12, 1983

[54] METHOD AND DEVICE FOR EXAMINING URINE FOR PARTICULATE CONSTITUENTS

[75] Inventors: Gert Schlueter, Liederbach; Wilhelm Schuster, Frankfurt am Main, both of Fed. Rep. of Germany

[73] Assignee: Battelle-Institut e.V., Frankfurt am Main, Fed. Rep. of Germany

[21] Appl. No.: 352,070

[22] Filed: Feb. 25, 1982

[30] Foreign Application Priority Data

Mar. 4, 1981 [DE] Fed. Rep. of Germany ....... 3108133

[51] Int. Cl.³ ..................... G01N 33/48; G01N 31/06
[52] U.S. Cl. ........................................ 436/63; 422/101; 422/102; 436/177; 436/178; 210/927
[58] Field of Search ................. 422/101, 102; 436/63, 436/177, 178; 210/927

[56] References Cited

U.S. PATENT DOCUMENTS

| | | | |
|---|---|---|---|
| 2,671,715 | 3/1954 | Beckley | 422/101 |
| 3,630,683 | 12/1971 | Robb | 422/101 X |
| 3,682,321 | 8/1972 | Smith | 422/101 X |
| 4,294,582 | 10/1981 | Naslund | 422/102 X |
| 4,321,139 | 3/1982 | Auclair | 422/101 X |
| 4,350,768 | 9/1982 | Tihon | 210/927 |

OTHER PUBLICATIONS

"Gradwohl's Clinical Laboratory Methods and Diagnosis", vol. 1, Sam Frankel et al., eds., 7th Edition, pp. 992-993, C. V. Mosby Co., Saint Louis, 1970.

Primary Examiner—Sidney Marantz
Attorney, Agent, or Firm—Fisher, Christen & Sabol

[57] ABSTRACT

To examine urine for particulate constituents, the urine is pased through a filter of synthetic fibers that are soluble in alcohol or in an alcohol-water mixture immediately after withdrawal. The filter material together with the constituents retained in it is then immediately dissolved in a cell-fixing solvent, in which it is protected from environmental influences and stored until it is examined.

An appropriate device for the implementation of this method consists of a urine collector and a filter cartridge which is fastened to the collector by a spring catch and can be detached after the urine has been passed through the filter, and connected liquid-tight with a storage vessel containing the solvent.

7 Claims, 2 Drawing Figures

METHOD AND DEVICE FOR EXAMINING URINE FOR PARTICULATE CONSTITUENTS

BACKGROUND OF THE INVENTION

1. Field of the Invention

The invention relates to a method and a device for examining urine for particulate constituents, in particular cells or crystalline substances. The examination of urine is of great importance for medical diagnostics, including medical check-ups.

2. Prior Art

In recent years the cytology of urine has gained increasing importance in the search for tumors in the urinary tract. This is certainly also due to the fact that preventive medicine provides for an increasing number of check-ups of persons who are susceptible to tumor formation, e.g., workers in the dye and rubber industries. Routine cytological methods are used not only for clarifying dysurias and hematurias of unknown origin but also for monitoring the development of carcinomas of the urinary bladder subjected to transurethral treatment. The same applies to radiotherapy, which is monitored by cytodiagnostics methods in the case of both urological and gynecological indications.

The cytology of urine is based on the investigation of exfoliating cells which have separated from the tissue and flaked off into the urine, and which are discharged in the urine. The cellular constituents of urine may originate from neoplasias of the kidneys and of the urinary tracts or from the walls of the urinary bladder, and may also result from inflammatory processes in the whole urogenital system. Further, it is possible that squamous epithelia from the genital tract are discharged in the urine of women, while cell material from the prostate gland may be discharged in the urine of men. Today, the urine samples for cytodiagnosis are taken by a specialist (urologist), or by a general practitioner if this is indicated, and submitted to a cytologist. They may be obtained by one of the following methods:

Spontaneous urine, normally morning urine, is collected by the patient who then brings it to the doctor;

Urine samples are withdrawn by means of catheters, for example if contamination of the sample with cells from the genital tract is to be avoided;

In special cases, cell material may be obtained from ureters and renal pelvis by catheterization or collected by cystoscopy.

The urine samples of different volume are sent to the cytological laboratory, either in native form or with a fixing agent, e.g., methanol acetic acid, having been added.

The cells are extracted from the urine sample by different methods, which depend in particular on the experience of the diagnostic laboratory concerned. The methods normally used at present are described below:

Production of a cell sediment by centrifugation. This means that urine samples between 2 and 10 ml in total volume are centrifuged, the supernatant is sucked off, and the sediment is processed into cell smears. If the concentration of cellular material in the urine is low, larger amounts of the urine sample submitted have to be distributed to several centrifuge tubes and processed separately, the individual sediments then being combined in one smear.

Some cytological laboratories usually process the urine samples by the cytocentrifuge. After shaking, 0.2 ml is drawn off and centrifuged; in this case a microscopic slide that is placed into the centrifuge is directly smeared with the cells.

When using the so-called filter technique, 10 mm of urine is poured into a filter head which is provided, for example, with millipore filters (pore size 5 $\mu$m). The liquid is sucked through the filter, and the cells are retained on the filter surface. The cells are then transferred from the filter to the microscopic slide, fixed and stained.

Which dyes are used for the urine sediment smears depends on the requirements of the method of visual diagnosis to be applied. The following staining method are normally used:

May-Gruenwald-Giemsa stain

Papanicolaou's stain

Methylene blue stain according to Löffler

All known methods have the drawback that the cells remain in the urine for a relatively long time, which renders diagnosis difficult because the cells undergo autolytic changes after a relatively short time. To ensure a reliable and correct diagnosis, it is therefore very important that the state of the cells immediately after collection be maintained. In practice, however, gynecological cytology tends to become a "mailing" process because for various reasons a large percentage of the samples to be examined has to be mailed to the laboratory. This means that during the time between collection and preparative treatment-i.e., 1 or 2 days or even longer-the urine samples are exposed to various influences which may render diagnosis difficult or render the result incorrect. Only in exceptional cases and under the most favorable conditions can the requirement be satisfied that a urine sample should be processed not later than two hours after collection, which is generally accepted by experts in the field.

Since a correct diagnosis result can only be achieved if the cells are well preserved, incorrect judgments in the evaluation or urine sediments are unavoidable with the conventional methods mentioned above. Depending on the properties and the composition of the urine, e.g., its pH value, cytolysis-which starts already in the urinary bladder-proceeds until the cell samples are fixed. However, satisfactory cell fixation is only achieved in an alcoholic medium of at least 70 percent; this is why in practice the alcohol cannot be added before cell collection, i.e., before separation of the urine.

BROAD DESCRIPTION OF THIS INVENTION

The basic advantages which the cytology of urine might have for the discovery of early neoplasias, for case controls or for the supervision of therapeutic measures will become effective only if the above-described drawbacks can be overcome; this is the objective of the present invention.

It has been found that the above problems can be solved according to the present invention if, in a procedure as described in the foregoing, the urine is passed through a filter of synthetic fibers that are soluble in alcohol or in an alcohol-water mixture discharge or withdrawal, and if subsequently, i.e., shortly afterwards, the fibers are dissolved in a cell-fixing solvent, and if the specimen, i.e., the cells obtained by filtration, are stored in this solvent until they are examined.

The method according to the invention ensures that almost all the cells or other particulate constituents contained in the urine are collected in a very simple manner and are then available for further examination. Fixation of the cells immediately after dissolution of the filter material ensures that the cytologist has an optimum specimen for examination and diagnosis, even after relatively long transport and storage times. Cell losses and damages, which cannot be avoided with the conventional techniques (centrifugation, filtering), will not occur. In practice it will no longer be necessary to take additional urine samples or repeat cell examinations, because even extended storage periods and inappropriate transport will not result in damages or incorrect results. Because of its simplicity and reliability, the method according to the invention is optimally suited also to mass medical check-ups.

According to an advantageous embodiment of the invention, a staining agent is added to the cell-fixing solvent.

The method according to the invention is best carried out with a device which consists essentially of a urine collector and a detachable filter cartridge fixed to this collector. The filter cartridge contains synthetic fibers that are soluble in alcohol or in an alcohol-water mixture as filter material and can be connected to the collector liquid-tight after filtration, i.e., after the urine has passed through the filter. The second opening of the filter cartridge is suitably dimensioned such that it can be closed by the cover of the collector, which may be a beaded rim bottle. The cover is removed prior to mounting the filter cartridge. The collector and filter cartridge are preferably connected by a spring catch.

DETAILED DESCRIPTION OF THIS INVENTION

Figure 1:
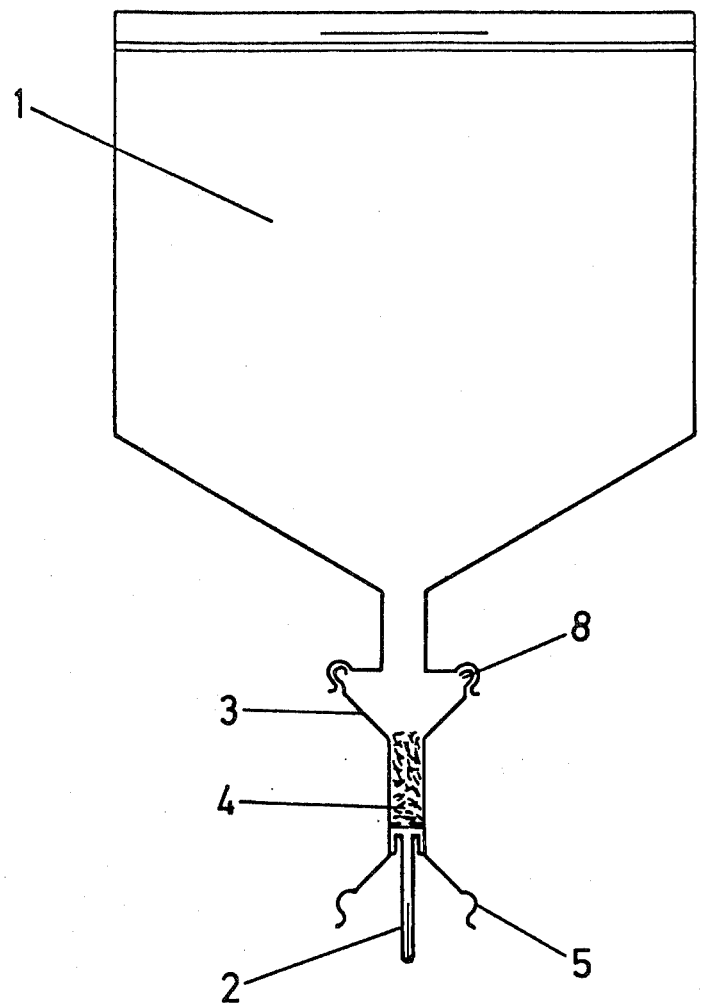

Additional features, advantages and potential applications can be gathered from the following description of further details, which is based on the attached diagrammatic representations.

Figure 2:
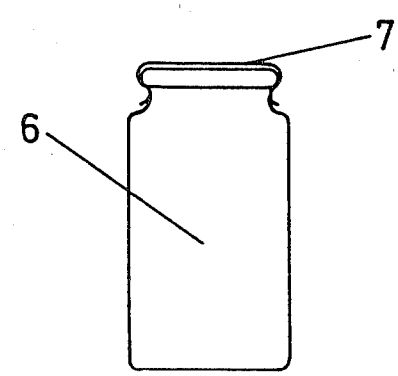

In the drawing:

FIG. 1 shows a device according to one embodiment of the invention which consists of a collector and a filter cartridge; and FIG. 2 shows a storage vessel for the device according to FIG. 1.

In the embodiment of the invention shown in FIG. 1, the device for the implementation of the method consists essentially of collector 11, which is a plastic bag for collecting the urine, and of filter cartridge 3, which is connected to collector 1 liquid-tight, but is detachable. In this embodiments the connection between vessel 1 and cartridge 3 is established by a spring catch, which is represented symbolically. Filter cartridge 3 contains filter 4 composed of synthetic fibers which are soluble in alcohol or in an alcohol-water mixture.

The most appropriate procedure is that the urine is collected in collector 1, which is then suspended above a drain. After removal of seal 2, collector 1 is drained, the urine sample being collected in filter 4. After the urine has passed through the filter, filter cartridge 3 is detached from vessel 1, and the lower part of filter cartridge 3, which is also designed as a spring catch, is placed on storage vessel 6, e.g., a beaded rim bottle, so that a sufficiently liquid-tight connection is established by spring-type part 5 catching the rim of the bottle. The cap of beaded rim bottle 6, which is previously used as cover 7, is then placed on the corresponding upper end 8 of filter cartridge 3, so that a liquid-tight connection is formed also at this point.

Storage vessel 6 contained a cell-fixing solvent, i.e., alcohol or an alcohol-water mixture, already before filter cartridge 3 is mounted. When storage vessel 6, filter 3 and cover 7 have been connected to form a liquid-tight unit, the filter material is mixed with the alcohol or the alcohol-water mixture by repeated shaking or tilting of the unit, so that filter material 4 is dissolved and the specimen, i.e., the cells separated by filtration, are fixed at the same time.

The filtering process, the dissolution of the fibers and the simultaneous fixation of the specimen take only a few minutes, so that after a short period of time a concentrated and fixed specimen is available in storage vessel 6, which can be mailed, stored and evaluated without excessive haste. The cell material contained in the alcoholic solution is then processed at the desired time and in the usual manner.

Microscopic examination of the material separated by filtration, e.g., cells, normally requires staining. According to the invention, this can be done in a very advantageous and economical manner by adding stains, e.g., methylene blue, to the alcoholic fixing and dissolving agent. Depending on the stain selected, cell-specific color reactions are feasible.

As the collection method according to the invention is very simple, it is possible for patients to apply it at home or elsewhere and without expert assistance. Preparing and mailing the sample, e.g., to the cytological laboratory, is easy; even unexperienced persons can filter the urine without the risk of altering or contaminating the sample, so that the cell specimen is then available in concentrated form and has a small volume. Since the filter material is contained inside the filter cartridge and since the method according to the invention ensures that it does not come into contact with the environment the specimen cannot be contaminated.

I claim:

1. Method of examining urine for particulate constituents comprising:
   (a) passing voided or withdrawn urine through a filter of synthetic fibers to capture said particulate constituents, said synthetic fibers being soluble in alcohol or in aqueous alcohol;
   (b) contacting the synthetic fibers resulting from step (a) with alcohol or aqueous alcohol to simultaneously dissolve the synthetic fibers and to fix the particulate constituents whereby an examinable specimen is obtained; and
   (c) storing the examinable specimen resulting from step (b) until the specimen is examined.

2. The method of claim 1 wherein the particulate constituents are cells.

3. Method as claimed in claim 1 wherein a cytopigment is added to the alcohol or aqueous alcohol.

4. Device for carrying out the method of examining urine for particulate constituents, the device consists essentially of (a) a urine collector, and (b) a detachable filter cartridge, which is affixed to said collector, said filter cartridge containing, as filter material, synthetic fibers that are soluble in alcohol or in aqueous alcohol, after the urine has passed through the filter, and after the collector has been removed, a liquid-tight connection is establishable between one opening of the filter cartridge and a storage vessel and the other opening is closable in a liquid-tight manner.

5. Device as claimed in claim 4 wherein the outlet of the filter cartridge is placed on the storage vessel and the inlet of the filter cartridge is sealed with the cover of the storage vessel.

6. Device as claimed in claim 5 wherein the storage vessel is a beaded rim bottle and the filter cartridge is connected with the vessel by a spring catch.

7. Device as claimed in claim 4 wherein the storage vessel is a beaded rim bottle and the filter cartridge is connected with the vessel by a spring catch.

* * * * *